United States Patent
Funk et al.

(10) Patent No.: US 12,303,658 B2
(45) Date of Patent: May 20, 2025

(54) SUPPORT DEVICES FOR BODILY FLUID TRANSFER SYSTEMS AND METHODS OF USING THE SAME

(71) Applicant: Velano Vascular, Inc., San Francisco, CA (US)

(72) Inventors: Brian Funk, San Francisco, CA (US); Pitamber Devgon, Philadelphia, PA (US)

(73) Assignee: Velano Vascular, Inc., San Francisco, CA (US)

( * ) Notice: Subject to any disclaimer, the term of this patent is extended or adjusted under 35 U.S.C. 154(b) by 0 days.

(21) Appl. No.: 18/618,533

(22) Filed: Mar. 27, 2024

(65) Prior Publication Data

US 2024/0238566 A1   Jul. 18, 2024

Related U.S. Application Data

(63) Continuation of application No. 17/698,550, filed on Mar. 18, 2022, now Pat. No. 11,969,562, which is a
(Continued)

(51) Int. Cl.
   *A61M 25/06* (2006.01)
   *A61B 5/15* (2006.01)
   (Continued)

(52) U.S. Cl.
   CPC ..... *A61M 25/0662* (2013.01); *A61B 5/15003* (2013.01); *A61B 5/150992* (2013.01);
   (Continued)

(58) Field of Classification Search
   CPC .......... A61M 25/0075; A61M 25/0062; A61M 25/0097; A61M 25/0102;
   (Continued)

(56) References Cited

U.S. PATENT DOCUMENTS 5,465,938 A   11/1995   Werge et al.
5,535,785 A    7/1996   Werge et al.
(Continued)

FOREIGN PATENT DOCUMENTS

| WO | 2004089437 A2 | 10/2004 |
| WO | 2016081008 A1 | 5/2016 |
| WO | 2017074674 A1 | 5/2017 |

*Primary Examiner* — Tasnim Mehjabin Ahmed
(74) *Attorney, Agent, or Firm* — The Webb Law Firm

(57) ABSTRACT

An access device including a lumen-defining device defining a lumen extending between a proximal end and a distal end, a support member disposed within the lumen of the lumen-defining device, and a hub configured to be coupled to the lumen-defining device and the support member. The support member and the lumen-defining device are flexible. When the lumen-defining device and the support member are bent, the support member supports at least a portion of the lumen-defining device without occluding or blocking the entire lumen and/or the support member is transitionable from a first configuration in which a proximal end portion of the support member extends in a first direction to a second configuration in which the proximal end portion extends in a second direction.

20 Claims, 8 Drawing Sheets

Related U.S. Application Data continuation of application No. 16/233,801, filed on Dec. 27, 2018, now Pat. No. 11,305,097.

(60) Provisional application No. 62/610,598, filed on Dec. 27, 2017.

(51) Int. Cl.
*A61B 5/153* (2006.01)
*A61M 25/00* (2006.01)
*A61M 25/01* (2006.01)

(52) U.S. Cl.
CPC ......... *A61B 5/153* (2013.01); *A61M 25/0075* (2013.01); *A61M 25/0097* (2013.01); *A61M 2025/0004* (2013.01); *A61M 2025/0079* (2013.01); *A61M 25/0102* (2013.01); *A61M 2025/0681* (2013.01); *A61M 2202/0413* (2013.01); *A61M 2210/12* (2013.01)

(58) Field of Classification Search
CPC .. A61M 2025/0079; A61M 2025/0681; A61M 2025/0004; A61M 2210/12; A61B 5/150992; A61B 5/150003; A61B 5/153
See application file for complete search history.

(56) References Cited

U.S. PATENT DOCUMENTS

| | | |
|---|---|---|
| 5,775,671 A | 7/1998 | Cote, Sr. |
| 5,807,350 A | 9/1998 | Diaz |
| 5,855,601 A | 1/1999 | Bessler et al. |
| 6,585,229 B2 | 7/2003 | Cote, Sr. et al. |
| 6,892,998 B2 | 5/2005 | Newton |
| 7,014,169 B2 | 3/2006 | Newton et al. |
| 7,357,792 B2 | 4/2008 | Newton et al. |
| 7,396,348 B2 | 7/2008 | Newton et al. |
| 7,789,864 B2 | 9/2010 | Cote, Sr. et al. |
| 7,887,519 B2 | 2/2011 | Cote, Sr. et al. |
| 8,100,869 B2 | 1/2012 | Vangsness et al. |
| 8,876,784 B2 | 11/2014 | Cote, Sr. et al. |
| 8,968,261 B2 | 3/2015 | Kimball et al. |
| 9,138,572 B2 | 9/2015 | Zeytoonian et al. |
| 9,604,047 B2 | 3/2017 | Newton et al. |
| 9,744,344 B1 | 8/2017 | Devgon et al. |
| 9,872,644 B2 | 1/2018 | Chelak et al. |
| 10,376,684 B2 | 8/2019 | Chelak et al. |
| 10,744,314 B2 | 8/2020 | Siopes et al. |
| D899,589 S | 10/2020 | Illsley |
| 10,806,901 B2 | 10/2020 | Burkholz et al. |
| 10,835,730 B2 | 11/2020 | Chelak et al. |
| 10,953,219 B2 | 3/2021 | Chelak et al. |
| 10,987,041 B2 | 4/2021 | Maseda et al. |
| 11,013,902 B2 | 5/2021 | Chelak et al. |
| 11,305,097 B2 | 4/2022 | Funk |
| 2004/0092872 A1 | 5/2004 | Botich et al. |
| 2006/0155244 A1 | 7/2006 | Popov |
| 2009/0192496 A1 | 7/2009 | Suwito et al. |
| 2009/0209922 A1 | 8/2009 | Boisjoly |
| 2010/0030164 A1 | 2/2010 | Kimball et al. |
| 2010/0030193 A1 | 2/2010 | Packard |
| 2010/0249725 A1 | 9/2010 | Cote, Sr. et al. |
| 2011/0202123 A1* | 8/2011 | Bonutti ............... A61M 25/065 604/27 |
| 2012/0220955 A1 | 8/2012 | Maseda et al. |
| 2012/0277627 A1* | 11/2012 | Devgon ........... A61B 5/150717 600/576 |
| 2017/0216564 A1 | 8/2017 | Devgon et al. |
| 2019/0070400 A1 | 3/2019 | Chelak et al. |
| 2021/0196940 A1 | 7/2021 | Damarati |
| 2021/0220548 A1 | 7/2021 | Kimball |
| 2021/0236777 A1 | 8/2021 | Chelak et al. |

\* cited by examiner

SUPPORT DEVICES FOR BODILY FLUID TRANSFER SYSTEMS AND METHODS OF USING THE SAME

CROSS-REFERENCE TO RELATED APPLICATIONS

This application is a continuation of U.S. patent application Ser. No. 17/698,550 entitled "Support Devices for Bodily Fluid Transfer Systems and Methods of Using the Same", filed Mar. 18, 2022, which is a continuation of U.S. patent application Ser. No. 16/233,801 entitled "Support Devices for Bodily Fluid Transfer Systems and Methods of Using the Same", filed Dec. 27, 2018 (now U.S. Pat. No. 11,305,097), which claims priority to and the benefit of U.S. Provisional Patent Application Ser. No. 62/610,598 entitled, "Support Devices for Bodily Fluid Transfer Systems and Methods of Using the Same", filed Dec. 27, 2017, the disclosures of each of which are incorporated herein by reference in their entirety.

BACKGROUND

The embodiments described herein relate generally to medical devices configured to be inserted into a patient. More particularly, the embodiments described herein relate to support devices configured to support lumen-defining devices, such as catheters, and/or configured to support anatomic structures in which the lumen-defining devices are at least partially disposed.

Many medical procedures and/or surgical interventions include inserting an access device or fluid transfer device into a portion of the body. For example, needles, catheters, and/or other lumen-defining devices can be inserted into and/or through vascular structures to access portions of the body and/or to transfer fluids to or from a patient. In general, rigid metal needles and/or trocars are percutaneously inserted into a patient to gain access to, for example, the patient's vein—allowing a relatively flexible lumen-defining device (e.g., a peripheral intravenous (PIV) catheter or the like) to be positioned within the vein. Once at least a portion of the lumen-defining device is disposed in the vein, the needle and/or trocar can be removed.

The use of the relatively flexible lumen-defining devices can increase patient comfort, reduce injury, and/or allow for extended indwelling times. In some instances, however, achieving sufficient access to a vein and/or sufficient fluid transfer to or from the vein can present challenges. For example, in some instances, the relatively flexible lumen-defining devices can become kinked, bent, and/or otherwise occluded, which can limit and/or substantially prevent fluid transfer and/or access therethrough. In other instances, the venous anatomy (e.g., venous wall thickness, valve and/or branch location relative to the insertion site, and/or the like) and/or characteristics of bodily fluid flow paths therethrough can limit and/or substantially prevent fluid transfer and/or access through the vein. For example, in some instances, aspiration through the lumen-defining device may result in a collapse or partial collapse of the vein and/or the lumen-defining device may be disposed in a compartment of the vein receiving limited bodily fluid flow.

Thus, a need exists for support devices configured to support lumen-defining devices, such as catheters, and/or configured to support anatomic structures in which the lumen-defining devices are at least partially disposed.

SUMMARY

Devices and methods for supporting lumen-defining devices, such as catheters, and/or supporting anatomic structures in which the lumen-defining devices are at least partially disposed are described herein. In some embodiments, a method includes disposing a lumen-defining device within a portion of a vein of a patient. A support member is inserted into a lumen of the lumen-defining device and advanced through at least a portion of the lumen of the lumen-defining device. At least a portion of the lumen-defining device is supported via the support member such that the support member limits complete occlusion of the lumen in response to a force exerted on the lumen-defining device. A volume of bodily fluid is withdrawn from the patient via the lumen-defining device when the support member is disposed in the lumen-defining device.

DETAILED DESCRIPTION

Figure 1A:
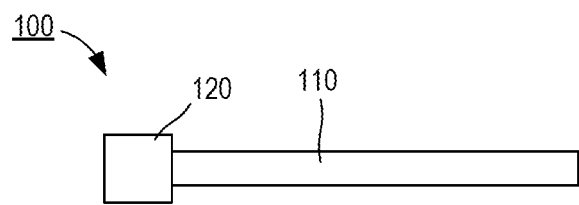
FIGS. 1A-1B and FIGS. 1C-1D are schematic illustrations of a known access device in a first configuration and a second configuration, respectively.
Figure 1B:
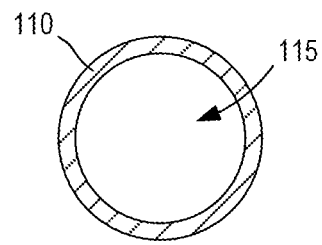

In some embodiments, a method includes disposing a lumen-defining device within a portion of a vein of a patient. A support member is inserted into a lumen of the lumen-defining device and advanced through at least a portion of the lumen of the lumen-defining device. At least a portion of the lumen-defining device is supported via the support member such that the support member limits complete occlusion of the lumen in response to a force exerted on the lumen-defining device. A volume of bodily fluid is withdrawn from the patient via the lumen-defining device when the support member is disposed in the lumen-defining device.

In some embodiments, a method includes establishing fluid communication between a lumen-defining device and a fluid source. A support member is coupled to a hub of the lumen-defining device such that a portion of the support member is disposed in a lumen of the lumen-defining device. At least a portion of the lumen-defining device is supported via the support member such that the support member limits complete occlusion of the lumen in response to a force exerted on the lumen-defining device. A fluid transfer device is coupled to the hub of the lumen-defining device and a volume of fluid is withdrawn from the fluid source into the fluid transfer device via the lumen-defining device when the support member is disposed in the lumen-defining device.

In some embodiments, a method includes disposing a lumen-defining device within a portion of a vein. A support member is inserted into a lumen of the lumen-defining device and advanced through the lumen of the lumen-defining device to a distal position such that at least a portion of the support member is disposed within the vein and distal to the lumen-defining device. The support member is transitioned from a first configuration to a second configuration after the support member is placed in the distal position. The support member configured to transition an anatomic valve within the vein from a substantially closed state to a substantially open state when the support member is in the distal position and in the second configuration.

In some embodiments, a method includes disposing a lumen-defining device such as, for example, a catheter, within a portion of a vein. A support member is inserted into the lumen-defining device and advanced through at least a portion of the lumen-defining device. The support member provides support to at least a portion of the lumen-defining device to limit complete occlusion of the lumen. The method can also include the support member being advanced into a portion of an anatomic structure such as a vein to provide support to the anatomic structure when the lumen-defined device is inserted into the anatomic structure.

In some embodiments, a method includes disposing a lumen-defining device such as, for example, a catheter, within a portion of a vein. A support member is inserted into the lumen-defining device and advanced through the lumen-defining device such that at least a portion of the support member is disposed within the vein and distal to the lumen-defining device. After the support member is placed in a desired position within the vein, the support member is transitioned from a first configuration to a second configuration. The support member transitions an anatomic valve within the vein from a substantially closed state to a substantially open state when the support member is transitioned from the first configuration to the second configuration.

The embodiments described herein can be used to facilitate and/or enhance the use of lumen-defining devices by providing support and/or other means for limiting and/or substantially preventing kinking or occlusion of the lumen-defining device. In some implementations, a lumen-defining device can be a cannula, catheter, conduit, access device, etc. used to provide access (e.g., to a portion of the body of a patient), transfer fluids, and/or the like. For example, in some embodiments, a device such as those described herein can be used to limit and/or substantially prevent occlusion of an access device or the like during surgical intervention and/or fluid transfer between a patient and any external connection, fluid source, fluid reservoir, etc. fluidically coupled to the access device. As one example, any of the embodiments (i.e., support devices) described herein can be used to support, for example, a peripheral intravenous line (PIV) (or other suitable access device or port) to limit and/or substantially prevent occlusion (e.g., substantially complete occlusion) of the PIV in response to the PIV being kinked, bent, and/or deformed. Thus, such support devices can support at least a portion of a lumen-defining device to facilitate the transfer of fluids between the patient and any external fluid source or external fluid collection device.

As another example, any of the embodiments (i.e., support devices) described herein can be used to support, for example, an anatomic structure such as a vein or portion of a vein to limit undesired deformation, constriction, collapse, etc. in response to being exposed to a negative pressure (e.g., a negative pressure during aspiration or the like). Similarly, such support devices can be used to remove obstructions within a vein and/or to transition a valve of the vein from a substantially closed configuration to a substantially open configuration. Thus, such support devices can support at least a portion of a vein and/or can remove or mitigate any flow restriction within the vein (e.g., obstruction, debris, valve, etc.) to facilitate the transfer of fluids between the patient and any external fluid source or external fluid collection device.

The embodiments herein are generally described as being used, for example, to facilitate the aspiration of a volume of bodily fluid (e.g., blood) from a patient. It should be understood, however, that the embodiments and/or devices are not limited to uses and/or procedures. For example, in some instances, the embodiments and/or devices can facilitate the aspiration of bodily fluid including but not limited to, blood, cerebrospinal fluid, urine, bile, lymph, saliva, synovial fluid, serous fluid, pleural fluid, amniotic fluid, mucus, vitreous, air, and the like, or any combination thereof. In other instances, the embodiments and/or devices can be used to facilitate the delivery of one or more fluids from a fluid source to the patient. In still other instances, the embodiments and/or devices can be used to facilitate any suitable procedure or the like involving catheterization of a target region in the body. That is to say, the embodiments and/or devices are not limited to transferring fluids to or from a patient and can be used, for example, to facilitate the process of gaining access to a target region in the body for any suitable purpose. While at least some of the devices are described herein as being used with and/or coupled to a PIV in order to transfer fluid to or from a patient, it should be understood that such use is presented by way of example only and not limitation. Moreover, it should be understood that reference to "a patient" need not be limited to a human patient. For example, any of the devices described herein can be used in any suitable procedure performed on an animal (e.g., by a veterinarian and/or the like).

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the terms "catheter" and "cannula" are used interchangeably to describe an element configured to define a passageway or lumen for accessing a portion of the body (e.g., of a human and/or animal). In some instances, the passageway defined by a catheter and/or cannula can be used for moving a bodily fluid or physical object (e.g., a stent, a guide wire, a punctate plug, a hyaluronic-acid-gel, etc.) from a first location to a second location. While cannulas can be configured to receive a trocar, a guide wire, or an introducer to deliver the cannula to a volume inside the body of a patient, the cannulas referred to herein need not include or receive a trocar, guide wire, or introducer. The terms "peripheral intravenous catheter" and "peripheral intravenous line" are likewise used interchangeably to describe a device configured to percutaneously access a vein via venipuncture.

As used herein, the term "indwelling" when characterizing a catheter or the like generally refers to a catheter that is at least partially disposed within a portion of the body. For example, an "indwelling peripheral intravenous catheter" (also referred to as "indwelling peripheral intravenous line," "PIV catheter," "PIV line," or "PIV") can be a peripheral intravenous catheter that is percutaneously inserted into the body and at least partially disposed within a vein. In general, the methods of using the devices and/or embodiments described herein can include inserting the devices into an indwelling peripheral intravenous catheter or can include inserting the devices in a peripheral intravenous catheter prior to being inserted into a portion of the body (e.g., prior to being "indwelling").

As used herein, the words "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

In some instances, the words "proximal" or "distal" can be used when describing relative terms and do not necessarily refer to universally fixed positions or directions. For example, a distal end portion of a PIV catheter can be inserted into a vein of a patient's forearm while a proximal end portion of the PIV catheter can be substantially outside of the body. Veins, however, carry a flow of oxygen-poor blood from distal portions of the body back to the heart and, as a result, PIV catheters are generally inserted into a vein such that a distal tip of the PIV catheter is disposed within the vein in a position proximal to the insertion point (e.g., extending relative to the vein in a proximal direction). Thus, a distal position relative to the PIV catheter can refer to, for example, a proximal position relative to the vein (e.g., closer to the heart).

As used herein, the term "stiffness" relates to an object's resistance to deflection, deformation, and/or displacement by an applied force. Stiffness can be characterized in terms of the amount of force applied to the object and the resulting distance through which a first portion of the object deflects, deforms, and/or displaces with respect to a second portion of the object. When characterizing the stiffness of an object, the deflected distance may be measured as the deflection of a portion of the object different from the portion of the object to which the force is directly applied. Said another way, in some objects, the point of deflection is distinct from the point where force is applied.

Stiffness is an extensive property of the object being described, and thus is dependent upon the material from which the object is formed as well as certain physical characteristics of the object (e.g., shape and boundary conditions). For example, the stiffness of an object can be increased or decreased by selectively including in the object a material having a desired modulus of elasticity, flexural modulus, and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the stiffness of the object can be increased, for example, by introducing into the object and/or constructing the object of a material having a high modulus of elasticity.

Similarly, a material's hardness is an intensive property of the constituent material and describes the measure of how resistant the material is to various kinds of permanent shape change when a force is applied. In discussing the hardness and the subsequent effect on the stiffness of a catheter, the Shore durometer scale is generally used. There are several scales for durometers with two commonly used in describing plastics, polymers, elastomers, and/or rubbers, namely, type A and type D, where type A is generally used for softer materials and type D is generally used for harder materials. The Shore durometer of a material is denoted by a number between 0 and 100, with higher numbers indicating a harder material, followed by the type of scale. For instance, a first material can be measured as having a Shore durometer of 40 Shore A and a second material can be measured as having a Shore durometer of 60 Shore D. Therefore, according to the Shore durometer scale, the second material is harder and thus, more stiff than the first material.

The embodiments described herein and/or portions thereof can be formed or constructed of one or more biocompatible materials. In some embodiments, the biocompatible materials can be selected based on one or more properties of the constituent material such as, for example, stiffness, toughness, durometer, bioreactivity, etc. Examples of suitable biocompatible materials include metals, glasses, ceramics, or polymers. Examples of suitable metals include pharmaceutical grade stainless steel, gold, titanium, nickel, iron, platinum, tin, chromium, copper, and/or alloys thereof. A polymer material may be biodegradable or non-biodegradable. Examples of suitable biodegradable polymers include polylactides, polyglycolides, polylactide-co-glycolides (PLGA), polyanhydrides, polyorthoesters, polyetheresters, polycaprolactones, polyesteramides, poly (butyric acid), poly(valeric acid), polyurethanes, and/or blends and copolymers thereof. Examples of non-biodegradable polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, and/or blends and copolymers thereof.

Figure 1C:
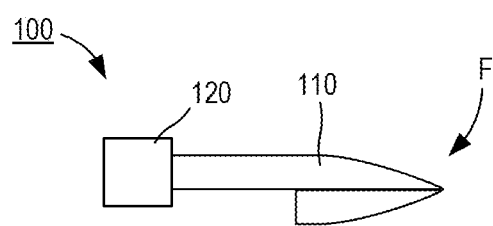
Figure 1D:

FIGS. 1A-1D are schematic illustrations of a known access device 100 (indicated by the label "Related Art" in FIGS. 1A-1D) in a first configuration (FIGS. 1A and 1B) and a second configuration (FIGS. 1C and 1D). The access device 100 (also referred to herein as "device") can be any suitable device configured to be at least partially inserted or disposed within a portion of the body. For example, the device 100 can be a peripheral intravenous line (PIV) or the like configured to be percutaneously inserted into a portion of the body. More specifically, the device 100 (e.g., PIV) can be at least partially disposed within a vein of a patient via a venipuncture event or the like, as described in further detail herein.

As shown in FIGS. 1A-1D, the device 100 includes a catheter 110 and a hub 120. The hub 120 can be any suitable device, mechanism, and/or member configured to allow access to a lumen 115 defined by the catheter 110. In some examples, the hub 120 is configured to selectively provide access to the lumen 115 of the catheter 110. For example, the hub 120 can be a port, lock (e.g., a Luer-Lok™), coupler, fitting, etc. As such, the hub 120 can be similar to or substantially the same as hubs included in known PIV devices. The catheter 110 can be formed of any suitable biocompatible material or combination of materials such as those described above. Moreover, the lumen 115 defined by the catheter 110 is in fluid communication with the hub 120. As such, the catheter 110 can be similar to or substantially the same as catheters included in known PIV devices. Accordingly, with the catheter 110 and the hub 120 being similar to or substantially the same as catheters and hubs, respectively, of known PIV devices, the device 100 itself is similar to and/or substantially the same as such known PIV devices.

In general, the catheter 110 of the device 100 is formed from a relatively soft material or combination of materials to allow the catheter 110 to bend, flex, and/or otherwise reconfigure (e.g., elastically or non-permanently). In some instances, such bending, flexing, and/or reconfiguring can be relatively minor such that the lumen 115 remains substantially open, allowing a flow of fluid therethrough. In other instances, however, a force (indicated by the arrow F in FIG. 1C) applied on the catheter 110 can be sufficient to kink and/or otherwise deform a portion of the catheter 110, which in turn, can result in a complete or substantially complete occlusion or obstruction of the lumen 115, as shown in FIGS. 1C and 1D. In such instances, the kinking and/or deforming can be the result of an angle of insertion into the vein, the catheter 110 impacting an obstruction, a negative pressure collapsing the catheter 110, and/or the result of any other reason. Moreover, the kinking and/or deforming of the catheter 110 can be such that the lumen 115 or a portion thereof is occluded and/or obstructed, which in turn, prevents or substantially prevents a flow of fluid therethrough.

While some known access devices 100 are prone to undesirable kinking, bending, collapsing, etc., as described above, in some instances, any suitable access device can be used with a support device configured to provide support to the access device to limit and/or substantially prevent undesired deformation and/or occlusion of the access device. For example, FIGS. 2A-2D illustrate an access device 200 and a support device 230, according to an embodiment. The access device 200 includes a catheter 210 and a hub 220. The catheter 210 defines a lumen 215 that is in fluid communication with the hub 220. The access device 200 can be any suitable access device or the like. For example, in some embodiments, the access device 200 can be similar to and/or substantially the same as the access device 100 described above with reference to FIGS. 1A-1D. In other words, the access device 200 can be, for example, a known access device such as a PIV or the like. Accordingly, the access device 200 is not described in further detail herein.

In some instances, any suitable access device such as a PIV can be coupled to and/or can otherwise engage a support device. For example, as shown in FIGS. 2A-2D, the access device 200 is coupled to, engages, and/or receives the support device 230. The support device 230 can be any suitable device, member, mechanism, etc. configured to provide support to at least a portion of the access device 210. For example, in some embodiments, the support device 230 can include a support member 235 and a hub 240. The hub 240 is configured to at least temporarily couple to the hub 220 of the access device 200. For example, the hub 240 can be a coupler or the like having a distal end portion configured to couple to the hub 220 and a proximal end portion configured to couple to any other suitable device. Moreover, the hub 240 can define a port, lumen, channel, and/or the like configured to allow a member or device to pass therethrough and/or configured to allow a flow of fluid to be transferred therethrough. As such, the hub 240 can couple to the hub 220 of the access device 200 without blocking and/or preventing access to the access device 200.

Figure 2A:
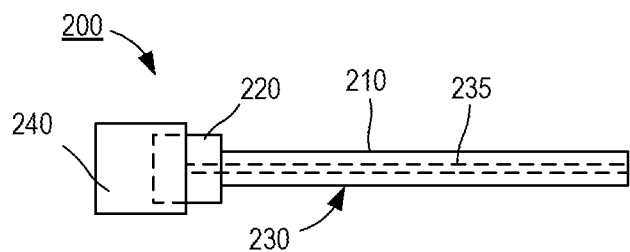
FIGS. 2A-2B and FIGS. 2C-2D are schematic illustrations of an access device and a support device, in a first configuration and a second configuration, respectively, according to an embodiment.
Figure 2B:
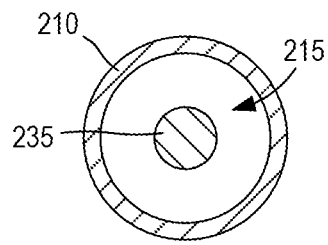

The support member 235 of the support device 230 is coupled to the hub 240 and is configured to be at least partially disposed within the catheter 210 of the access device 200 when the hub 240 of the support device 230 is coupled to the hub 220 of the access device 200, as shown in FIG. 2A. The support member 235 can be any suitable shape, size, and/or configuration and can be formed of any suitable material or combination of materials. For example, as shown in FIGS. 2A-2D, the support member 235 can have a size and/or shape that allows the support member 235 to be disposed within the catheter 210 of the access device 200 without occluding and/or blocking the entire lumen 215 of the catheter 210. In other words, the support member 235 can have a diameter and/or perimeter that is smaller than an inner diameter or inner perimeter of the catheter 210 (see e.g., FIG. 2B). In this manner, when the support device 230 is coupled to the access device 200, the access device 200 can still provide access to a portion of the body.

In some embodiments, the size of the support member 235 can be at least partially based on a size of the catheter 210. For example, in some embodiments, an access device (e.g., the access device 200) can include a catheter (e.g., a catheter 210) that is, for example, a 16-gauge catheter. A support device (e.g., the support device 230) configured for use with such an access device can include a support member (e.g., the support member 235) that has a size and/or diameter that is substantially smaller than an inner diameter of the 16-gauge catheter. In other embodiments, a catheter can be, for example, a 24-gauge catheter and a support member configured for use with such a catheter can have a size and/or diameter that is substantially smaller than an inner diameter of the 24-gauge catheter. Moreover, the size and/or diameter of the support member configured for use with the 24-gauge catheter can be smaller than the size and/or diameter of the support member configured for use with the 16-gauge catheter. In other words, in some embodiments, the size, shape, and/or configuration of the support device 230 can be based at least in part on the size, shape, and/or configuration of the access device 200 that the support device 230 is configured to support.

As described above, the support member 235 can be formed of or from any suitable material or combination of materials. For example, in some embodiments, the support member 235 can be formed of a relatively flexible material such as plastic, nylon, rubber, and/or any other suitable material such as those described herein. In some embodiments, the support member 235 can be arranged as a filament or the like. In some embodiments, the support member 235 can have a durometer between about 20 Shore A to about 95 Shore D. As described above with reference to the size and/or configuration of the support member 235, in some embodiments, the support member 235 can have a stiffness and/or durometer that is at least partially based on a stiffness and/or durometer of the catheter 210 of the access device 200. For example, in some embodiments, the support member 235 can have a stiffness and/or durometer that is greater than a stiffness and/or durometer of the catheter 210 in which the support member 235 is disposed. While the support member 235 is described above as being formed of a plastic, nylon, rubber, etc., in some embodiments, the support member 235 can be formed of or from a shape memory alloy such as nickel-titanium (also referred to as "nitinol") and/or any other suitable material(s).

Figure 2C:
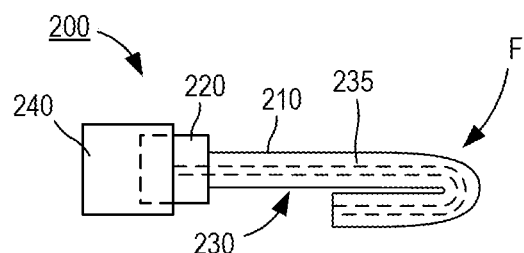
Figure 2D:
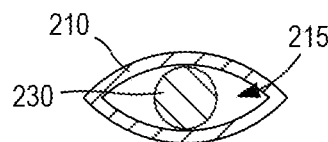

As shown in FIGS. 2C and 2D, the support member 235 is configured to support at least a portion of the catheter 210 when the support member 235 is disposed within the lumen 215. For example, as described above with reference to FIGS. 1C and 1D, the catheter 210 of the device 200 is formed from a relatively soft material or combination of materials to allow the catheter 210 to bend, flex, and/or otherwise reconfigure (e.g., elastically or non-permanently). In some instances, such bending, flexing, and/or reconfiguring in response to an applied force can be result in a complete or substantially complete occlusion or obstruction of the lumen or the catheter (see e.g., FIGS. 1C and 1D). With the support device 230 coupled to the access device 200, however, the support member 235 can provide support to the catheter 210 such that bending, flexing, and/or reconfiguring of the catheter 210 does kink the catheter 210 that results in a complete or substantially complete occlusion or obstruction of the lumen 215.

For example, as shown in FIGS. 2C and 2D, a force can be exerted on the catheter 210 (represented by the arrow F in FIG. 2C) that would be sufficient to kink the catheter 210. With the support device 230 coupled to the access device 210, however, at least a portion of the force F is transferred to and/or exerted on the support member 235. In some embodiments, the support member 235 can have a stiffness and/or durometer that is sufficient to result in an elastic deformation of the support member 235 in response to the force F. Moreover, as shown in FIG. 2C, the force F exerted on the support member 235 can bend or flex a portion of the support member 235 with a relatively large or broad radius of curvature. That is to say, the support member 235 is configured to limit and/or prevent a kinking, folding, and/or buckling of the support member 235.

As shown in FIGS. 2C and 2D, the arrangement of the support member 235 within the catheter 210 can result in a broader or larger radius of curvature of the catheter 210 in response to the applied force F when compared to a radius of curvature of the catheter when the support member 235 is not disposed therein (e.g., as shown above with reference to the catheter 110 in FIGS. 1C and 1D). In other words, the presence of the support member 235 within the catheter 210 can limit and/or substantially prevent a kinking, folding, and/or buckling of the catheter 210 in response to the applied force F. Moreover, as shown in FIG. 2D, by limiting and/or substantially preventing kinking, folding, and/or buckling of the catheter 210, the support member 235 can also limit and/or substantially prevent a complete occlusion or substantially complete occlusion of the lumen 215 of the catheter 210. Accordingly, the support device 230 can be coupled to the access device 200 to limit and/or prevent kinking or the like that can otherwise result in an occlusion, obstruction, blockage, closing, etc. of the lumen 215 of the catheter 210.

Figure 3:
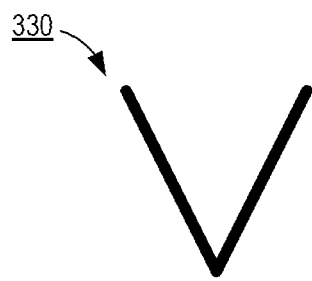
FIGS. 3-8 are cross-sectional schematic illustrations of various support devices each according to a different embodiment.
Figure 4:
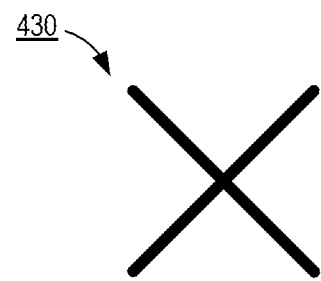
Figure 5:
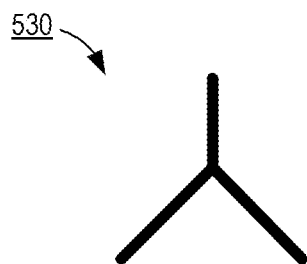
Figure 6:
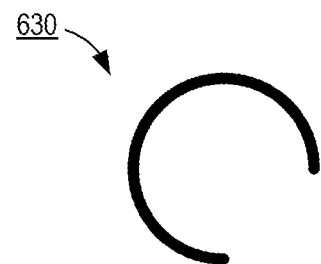
Figure 7:
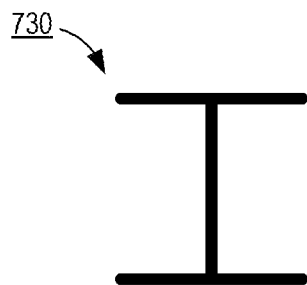
Figure 8:
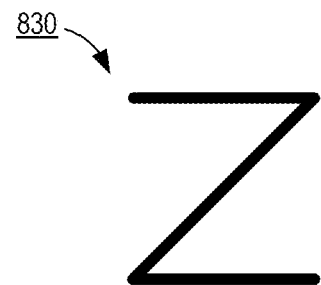

As described above the support member 235 of the support device 230 can have any suitable shape, size, and/or configuration. For example, as shown in FIG. 2A-2D, the support member 235 can be a substantially solid elongate member having a circular or at least semi-circular cross-sectional shape. In other embodiments, however, a support member can have any suitable shape and/or configuration. For example, FIGS. 3-8 are cross-sectional schematic illustrations of various support devices (or support members) each according to a different embodiment. Specifically, as shown in FIG. 3, a support device 330 and/or a support member of the support device 330 can have a substantially V-shaped cross-section; as shown in FIG. 4, a support device 430 and/or support member of the support device 430 can have a substantially X-shaped cross-section; as shown in FIG. 5, a support device 530 and/or support member of the support device 530 can have a substantially Y-shaped cross-section; as shown in FIG. 6, a support device 630 and/or support member of the support device 630 can have a substantially C-shaped cross-section; as shown in FIG. 7, a support device 730 and/or support member of the support device 730 can have a substantially I-shaped cross-section; and as shown in FIG. 8, a support device 830 and/or support member of the support device 830 can have a substantially Z-shaped cross-section.

In some embodiments, the size and/or cross-sectional shape of a support device and/or support member thereof can be based at least partially on the size, shape, and/or configuration of the access device that the support device is configured to support. In some embodiments, the size, shape, and/or configuration of a support device and/or a support member thereof can be designed and/or selected based on an amount of desired support to be provided to the access device. For example, in some embodiments, the varying the cross-sectional shape of a support device and/or support member thereof can, for example, vary a stiffness of the support device and/or support member. Moreover, in some instances, it may be desirable to use a support device and/or support member having a given cross-sectional shape based on a size and/or gauge of the catheter being supported. For example, in some instances, a support device and/or support member having a V-shaped cross-section (e.g., the support device 330 shown in FIG. 3) may provide a sufficient amount of support for a relatively small gauge catheter (or access device having a small gauge catheter) while occluding a relatively small portion of the lumen of the catheter. Conversely, in some instances, a support device and/or support member having a solid and circular cross-section (e.g., the support member 235) may provide a sufficient amount of support for such a relatively small gauge catheter but may occlude a relatively larger portion of the lumen of the catheter when compared to the support device and/or support member having the V-shaped cross-section.

While the support devices 230, 330, 430, 530, 630, 730, and 830 are particularly shown and described above as having and/or as including a support member having a specific cross-sectional shape, it should be understood, that the support devices 230, 330, 430, 530, 630, 730, and 830 have been presented by way of example only and not limitation. For example, in some embodiments, a support device and/or a support member can have any suitable cross-sectional shape in addition to those described herein. Moreover, a support device and/or support member can have a cross-sectional shape that is varied along a length thereof. For example, in some embodiments, a support device and/or support member can have a cross-sectional shape that tapers (e.g., is reduced in size) along a length of the support device in a proximal direction or in a distal direction. In other embodiments, a support device and/or support member can have a cross-sectional shape that is different at or near a proximal end thereof from a cross-sectional shape at or near a distal end thereof. In some embodiments, a support device and/or support member (or portion thereof) can form, for example, a spiral, coil, braid, and/or the like.

Although not shown in FIGS. 2A-2D and/or FIGS. 3-8, in some embodiments, a support device can include a support member that has a substantially annular cross-sectional shape similar to, for example, a catheter in which the support member is disposed. In some such embodiments, the support member can have an outer diameter that is slightly smaller than an inner diameter of the catheter in which the support member is at least partially disposed. In such embodiments, the support member and the catheter can collectively increase a wall thickness that can resist kinking of the catheter and support member. In some embodiments, the support device can have a substantially annular cross-sectional shape and can include one or more support portions spanning a lumen defined by the annular cross-sectional shape. For example, in some embodiments, a support device and/or a support member can be substantially similar to those shown in FIGS. 3-8 but can differ by including an annular ring that circumscribes the cross-sectional shapes shown in FIGS. 3-8.

While the support devices 230, 330, 430, 530, 630, 730, and 830 are described above as providing support for an access device (e.g., the access device 200), in other embodiments, a support device can be used with an access device and/or the like and can be configured to provide support to an anatomic structure in which the access device is at least partially disposed (e.g., to a vein or the like). For example, in some instances, the devices and methods described herein can be used for the aspiration of blood from a vein of a patient, which is accessed via an access device such as an indwelling peripheral intravenous (PIV) catheter. The cutaneous veins of the antecubital arm region, forearm, and hand are the most accessed sites for intravenous catheterization. It should be understood, however, that the devices and/or methods described herein are not limited thereto.

Figure 9:
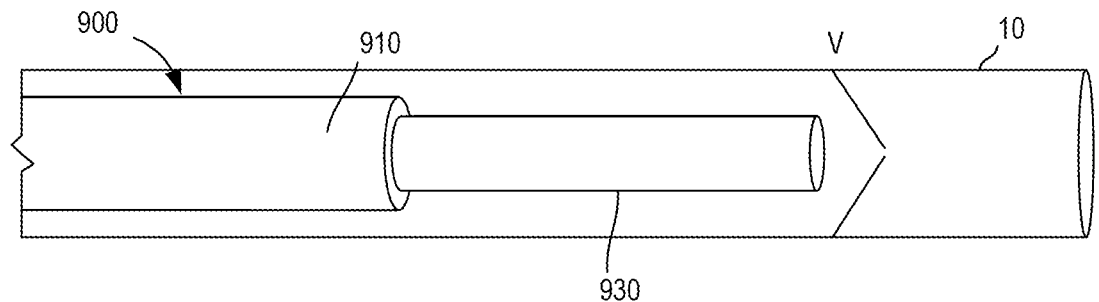
FIGS. 9 and 10 are schematic illustrations of a support device disposed in a vascular structure in a first configuration and a second configuration, respectively, according to an embodiment.
Figure 10:
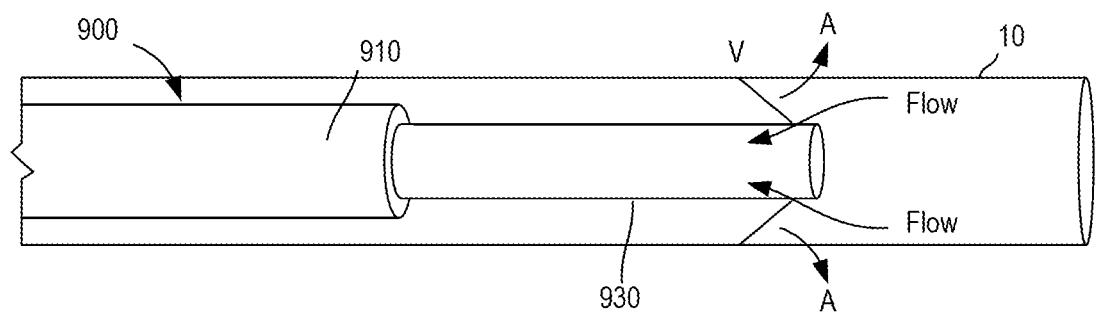

FIGS. 9 and 10 are schematic illustrations of a portion of an access device 900 and a portion of a support device 930 (also referred to herein as "support member") disposed within an anatomic structure, according to an embodiment. As shown, the access device 900 includes a catheter 910 configured to be at least partially inserted into an anatomic structure of a patient such as a vein 10 (e.g., a vein of the antecubital arm region, forearm, or hand). The access device 900 can be any suitable access device. For example, in some embodiments, the access device 900 can be similar to and/or substantially the same as the access devices 100 and/or 200 described above. More particularly, in some embodiments, the access device 900 can be, for example a PIV. The support device 930 can be any suitable support device. For example, in some embodiments, the support device 930 can be similar to and/or substantially the same as the support devices 130, 230, 330, 430, 530, 630, 730, and/or 830 described above. As such, portions of the access device 900 and/or the support device 930 are not described in further detail herein and should be considered as substantially similar in at least form and/or function to those described above unless otherwise indicated.

While the vein 10 is particularly shown in FIGS. 9 and 10, it should be understood that the arrangement of the vein 10 is presented by way of example and not limitation. As shown, the vein 10 defines a lumen and includes at least one valve V. The valve V disposed within the lumen of the vein 10 substantially controls at least a portion of blood flow through a section of the vein 10. For example, the valve V can transition and/or can be transitioned from an open configuration, in which blood can flow through at least a section of the vein 10, to a closed configuration, in which blood flow through the section of the vein 10 is limited, restricted, and/or substantially prevented. In some instances, the valve V is transitioned from an open configuration to a closed configuration in response to a negative pressure associated with and/or resulting from aspiration. In other instances, the valve V can transition in response to a presence of a portion of an access device. In still other instances, the valve can transition in response to any suitable naturally occurring event at, on, or in the vein 10.

When referring to the valve(s) V and/or any other valve(s) described herein it should be understood that the valve(s) can be anatomic structures within the vein 10 or can be any other suitable form of flow control serving a function similar to anatomical valves and/or acting in a valve-like manner to obstruct and/or control blood flow in one or more directions. For example, the vein 10 can include any number of anatomical valves formed of tissue and disposed in a given position within the vein 10 that control a flow of blood within the vein 10 (e.g., in a proximal direction or in a direction toward the heart). In other words, valve(s) V generally limit and/or substantially prevent a backflow of blood within the vein 10 (e.g., in a distal direction or in a direction away from the heart). Although not shown in FIGS. 9 and 10, the vein 10 can include and/or can be coupled to one or more branch vessels that can provide an inlet flow of blood into the vein 10 or can receive an outlet flow of blood from the vein 10. Moreover, the valve(s) V within the vein 10 can be positioned and/or otherwise can be configured to control such inlet and/or outlet flow from or into any suitable number of branch vessels (not shown).

In some instances, one or more of the valves V can transition between an open or closed configuration to, for example, divert a flow of blood through a branch and/or to otherwise control a flow of blood through the vein 10. In some instances, compartments defined between two adjacent valves V in the closed configuration or between a portion of an access device and a closed valve V can result in a significantly reduced flow of blood through that compartment. In some instances, a flow of blood can enter and/or exit a compartment defined by adjacent closed valves V via one or more branch vessels. In some instances, however, the catheter 910 may be inserted into the vein 10 such that a distal end of the catheter 910 is disposed within the vein 10 such that a compartment receiving and/or having a reduced flow of blood is defined between a portion of the catheter 910 and a closed valve V. Moreover, in some instances, the positioning of the catheter 910 within the vein 10 results in at least a partial occlusion of the lumen of the vein 10. That is to say, the presence of the catheter 910 within the vein 10 reduces and/or restricts a flow of blood around the catheter 910.

In the example shown in FIG. 9, the catheter 910 can be inserted into the vein 10 such that a distal end portion of the catheter 910 defines a first end of a compartment and the valve V defines a second end of the compartment. In some instances, the placement of the catheter 910 and the configuration of the valve V (e.g., in a substantially closed state or a state in which flow is at least partially limited) is such that the compartment receives a limited flow of blood. In some instances, the valve V can be in a substantially open state and in response to aspiration through the catheter 910, the valve V can be transitioned to the substantially closed state. In some instances, the flow of blood through the compartment can be reduced despite the compartment receiving a flow of blood from one or more branch vessels and/or regardless of the position of the distal end of the catheter 910 relative to the one or more branch vessels. In some instances, for example, the flow of blood into the compartment can be reduced by about 10%, about 20%, about 30%, about 40%, about 50%, about 60%, about 70%, about 80%, about 90%, or about 99%. In other instances, the presence of the catheter 910 can restrict the flow of blood through the compartment by 100%. In still other instances, the presence of the PIV 180 can restrict the flow of blood through the compartment by less than 10%.

In general, peripheral intravenous catheters such as the catheter 910 can be used to infuse fluids into the body but are not typically used to aspirate blood because of, for example, poor blood return ability (especially as indwelling time increases), debris surrounding the distal tip of the catheter 910, kinks in the catheter 910, hemolysis of blood samples, vein collapse, and/or the like. As described above, the catheter 910 can receive a support device (such as those described herein) that can limit and/or substantially prevent kinking of the catheter 910 that might otherwise occlude the catheter 910 and/or that might otherwise prevent aspirating blood through the catheter 910. In the embodiment shown in FIGS. 9 and 10, the support device 930 can be inserted into and advanced through the catheter 910 to provide support to the vein 10, which in turn, can limit and/or substantially prevent vein collapse, low blood flow through one or more compartments, valve closure, and/or the like.

For example, in the example shown in FIGS. 9 and 10, the support device 930 (or support member) can be advanced through a portion of the vein 10 such that at least a portion of the support device 930 extends through the valve V. As such, the support device 930 can exert a force that can transition the valve V from a closed state (FIG. 9) to an open state (as indicated by the arrows A in FIG. 10). The opening of the valve V, in turn, can allow a flow of blood to be drawn into the compartment that otherwise was receiving low blood flow. More particularly, the support device 910 can act to open, support, and at least temporarily maintain the valve V in an open state (FIG. 10), which in turn, can allow blood to flow into the compartment and the catheter 910 in response to a negative pressure exerted through the catheter 910 (i.e., in response to a negative pressure associated with and/or produced by aspirating via the catheter 910). Thus, the support device 930 can be configured to support at least a portion of the vein 10 (e.g., the valve 10) to allow for a flow of blood into the catheter 910 that is sufficient for aspiration.

While the vein 10 is described as including the anatomic valve V that controls the flow of blood through at least a portion of the vein 10, in some instances, an event can trigger and/or otherwise can result in a valve-like response within a portion of the vein 10 that can selectively control a flow of blood through that portion. For example, in some instances, a vasospasm of a portion of the vein 10 can result in a constriction of the lumen defined by the portion of the vein 10 that is sufficient to restrict and/or otherwise limit a flow of blood therethrough (e.g., in a proximal and/or a distal direction). In such instances, a relaxing of the portion of the vein 10 after the vasospasm can result in a dilation of the vein 10 and/or otherwise can result in a return to a non-spastic arrangement, which in turn, removes the limitation on the blood flow resulting from the vasospasm. As such, the occurrence of a vasospasm along a portion of the vein 10 can effectively result in a valve-like response within that portion of the vein 10 that is sufficient to selectively control (e.g., limit or obstruct) a flow of blood therethrough.

In some instances, the presence of, for example, the catheter 910 of the access device 900 within the vein 10 and/or a contact between a portion of the catheter 910 and a portion of the vein wall can result in a vasospasm of at least a portion of the vein 10. In other instances, a vein, debris (e.g., thrombus), muscle response, constriction, and/or any other structure, event, and/or response can act in a valve-like function within the vein 10 and/or can otherwise restrict a flow of blood through the vein (e.g., in a proximal and/or distal direction within the vein 10). By way of example, the flexing of a muscle, the bending of a joint or appendage (e.g., elbow, arm, fingers, etc.), the presence of an externally applied force (e.g., pressure applied by a blood pressure cuff, pressure applied by a medical professional's hand or finger (s), pressure applied by an ultrasound probe), coughing or valsalva resulting in a temporary reversal of blood flow, injection of substances resulting in vaso-inflammation, and/or the like. In such instances, inserting the support device 930 through the catheter 910 and into the vein 10 can limit and/or can substantially prevent a complete occlusion of the lumen of the vein 10 during the vasospasm and/or other valve-like response(s). Because the support device 930 has a smaller diameter and/or size than the catheter 910 (as described above), the support device 930 can prevent a complete occlusion of the lumen of the vein 10 without causing and/or otherwise without resulting in further vasospasm and/or the like. Thus, the support device 930 can allow an amount of blood to flow through at least a portion of the vein 10 and into the catheter 910 that is sufficient for aspiration.

Figure 11:
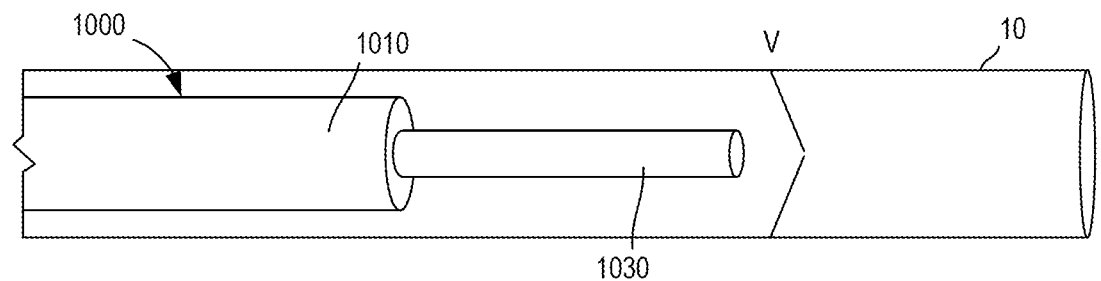
FIGS. 11 and 12 are schematic illustrations of a support device disposed in a vascular structure in a first configuration and a second configuration, respectively, according to an embodiment.
Figure 12:
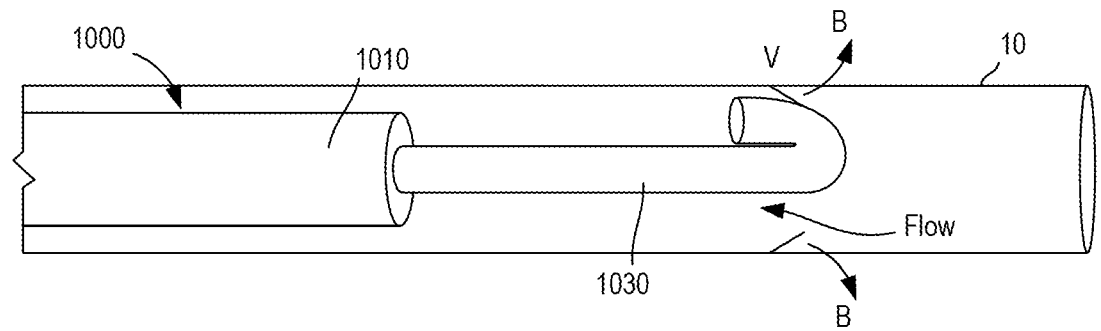

While the support device 930 is shown in FIGS. 9 and 10 as maintaining a substantially constant shape while being advanced in a proximal direction and/or a distal direction within the vein 10, in other embodiments, a support device can be configured to transition between any suitable number of shapes, states, modes, configurations, etc. For example, FIGS. 11 and 12 are schematic illustrations of a portion of an access device 1000 and a portion of a support device 1030 disposed within the vein 10, according to an embodiment. As shown, the access device 1000 includes a catheter 1010 configured to be at least partially inserted into the vein 10. As described above with reference to FIGS. 9 and 10, the access device 1000 can be any suitable device for accessing a portion of the patient such as those described herein. For example, in some embodiments, the access device 1000 can be a PIV and/or the like. Accordingly, the access device 1000 is not described in further detail herein.

The support device 1030 can be any suitable support device. For example, in some embodiments, the support device 1030 can be substantially similar in at least form and/or function to any of the support devices described above. For example, as described above with reference to the support device 930, the support device 1030 can be advanced through a portion of the vein 10 such that at least a portion of the support device 1030 is in close proximity to the valve V and/or such that a portion of the support device 1030 extends through the valve V. The support device 1030, however, can differ from the support device 930 in that when the portion of the support device 1030 is positioned at or near the valve V, the support device 1030 can be manipulated to transition from a first configuration or state (FIG. 11) to a second configuration or state (FIG. 12). For example, in some embodiments, the support device 1030 and/or at least a portion of the support device 1030 can be formed of a reconfigurable material. Such a reconfigurable material can be a material that is biased or previously deformed and can be in and/or can have first shape when constrained and can be in and/or have a second shape when unconstrained. In some embodiments, the support device 1030 can be formed from a shape-memory alloy or the like such as nickel-titanium (nitinol) and/or the like. As shown in FIG. 11, the support device 1030 can be advanced through the catheter 1010 and a portion of the vein 10 while in the first configuration or state and once a portion of the support device 1030 is in a desired position relative to the valve V, the support device 1030 and/or a portion of the support device 1030 can be transitioned to the second configuration and/or state (FIG. 12).

In some embodiments, the support device 1030 can be configured to bend, flex, and/or deform when the support device 1030 is transitioned from the first configuration or state to the second configuration or state. For example, a distal end portion of the support device 1030 can be reconfigured from the first configuration and/or state in which a central axis (not shown) extends through a distal end surface in a first direction, to a second configuration and/or state in which the central axis extends through the distal end surface in a second direction different from the first direction. In some embodiments, the distal end portion of the support device 1030 can be configured to form a U-bend such that a portion of the support device 1030 folds and/or bends to place the distal end surface of the support device 1030 in an opposite, reversed, and/or proximal direction. Said another way, at least a portion of the support device 1030 can form a 180° turn or bend.

The support device 1030 can be positioned within the vein 10 such that the bent, flexed, folded, deformed, and/or reconfigured portion of the support device 1030 is in a desired position relative to the valve V. In some instances, for example, the reconfigured portion of the support device 1030 can be at least partially disposed within the valve V to transition the valve V from a first configuration or state (e.g., a substantially closed state, as shown in FIG. 11) to a second configuration or state (e.g., a substantially open state, as shown in FIG. 12). In other words, the reconfiguring and/or transitioning of the portion of the support device 1030 from the first configuration to the second configuration can be operable to transition the valve V from a closed state to an open state, as indicated by the arrows B in FIG. 12. As described above, when the support device 1030 places the valve V in the open state, a flow of blood can be allowed to flow through the valve and into the compartment of the vein 10 in which the catheter 1010 is disposed. Thus, the support device 1030 can support at least a portion of the vein 10 (e.g., the valve 10) to allow for a flow of blood into the catheter 1010 that is sufficient for aspiration.

While the support device 1030 is described above as being formed of a deformable material such as, for example, nitinol, in other embodiments, the support device 1030 can be formed of any suitable material or combination of materials. In some embodiments, the support device 1030 and/or at least a portion of the support device 1030 can be steerable and/or can be deformed in response to an actuator or the like. In such embodiments, the actuator can be a tether or the like configured to exert a force on a portion of the support device 1030 that is sufficient to transition the support device 1030 from the first configuration to the second configuration. In other embodiments, the support device 1030 can be configured to transition in response to any suitable actuation (e.g., temperature-based, pressure-based, fluid-based, time-based, etc.). For example, in some embodiments, the support device 1030 can be configured to transition from the first configuration to the second configuration in response to an increase in temperature as a result of being disposed in the vein 10. In other words, such a support device can be configured to transition in response to a temperature within the vein being warmer than a temperature outside of the body and/or a temperature within the catheter 1010. In other embodiments, a portion of the support device 1030 can be wetted and/or saturated by a volume of blood within the vein 10, which in turn, can be operable to actuate the support device 1030.

While the support device 1030 and/or a portion thereof is shown in FIGS. 11 and 12 as being transitioned from the first configuration to the second configuration by deforming, deflecting, bending, and/or reconfiguring in a particular manner, in other embodiments, a support device can be inserted into a portion of a vein and placed in a configuration having any suitable arrangement. For example, FIGS. 13-16 are schematic illustrations of a portion of an access device 1100 and a portion of a support device 1130 disposed within the vein 10, according to an embodiment. As shown, the access device 1100 includes a catheter 1110 configured to be at least partially inserted into the vein 10. As described above with reference to FIGS. 9 and 10, the access device 1100 can be any suitable device for accessing a portion of the patient such as those described herein. For example, in some embodiments, the access device 1100 can be a PIV and/or the like. Accordingly, the access device 1000 is not described in further detail herein.

The support device 1130 can be any suitable support device. For example, in some embodiments, the support device 1130 can be substantially similar in at least form and/or function to any of the support devices described above. For example, as described above with reference to the support device 1030, the support device 1130 can be advanced through a portion of the vein 10 such that at least a portion of the support device 1130 is in close proximity to the valve V and/or such that a portion of the support device 1130 extends through the valve V. Moreover, the support device 1130 can be configured to transition from a first configuration or state to a second configuration or state, as described above with reference to the support device 1030.

The support device 1130 can differ from the support device 1030, however, in the arrangement of the support device 1130 when placed in the second configuration or state. For example, the support device 1130 can be inserted through the catheter 1110 and into a portion of the vein when the support device 1130 is in a first configuration or state (not shown in FIGS. 13-16). As described above, the support device 1130 can have a relatively straight or otherwise undeformed arrangement when in the first configuration or state. When a desired portion of the support device 1130 is disposed in the vein 10, the support device 1130 can be transitioned from the first configuration or state to the second configuration or state. As shown in FIGS. 13-16, the support device 1130 can have a waved arrangement (e.g., an oscillating arrangement with one or more local maxima and one or more local minima) when in the second configuration or state.

Figure 13:
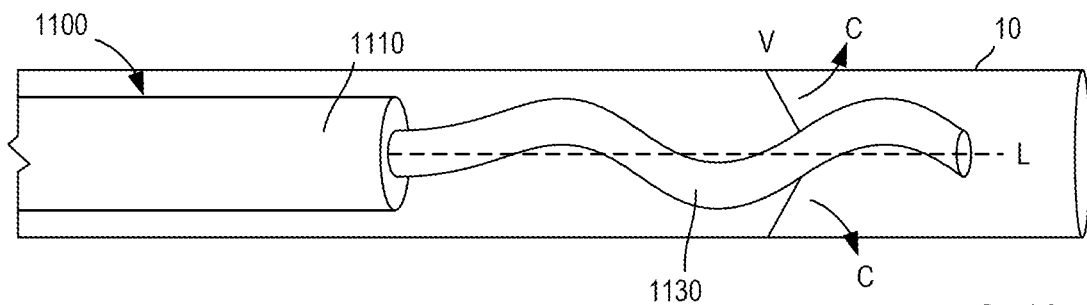
FIGS. 13 and 15 are schematic illustrations of a support device disposed in a vascular structure in a first position relative to the vascular structure and a second position relative to the vascular structure, respectively, according to an embodiment.
Figure 14:
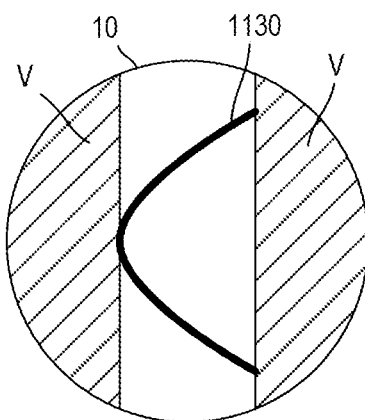
FIGS. 14 and 16 are cross-sectional schematic illustrations of the support devices shown in FIG. 13 and FIG. 15, respectively.

When in the second configuration or state, the support device 1130 can be positioned relative to the valve V to support the valve V and/or to transition the valve V from a closed state to an open state, as described above. In the embodiment shown in FIG. 13-16, the arrangement of the support device 1130 in the second configuration can be such that adjusting a position of the support device 1130 relative to the vein can result in an increase or decrease in an amount of support provided by the support device 1130, which in turn, can result in an increase or decrease, respectively, in an amount of displacement of the valve V. For example, the support device 1130 can be inserted through the catheter 1110 and into the vein 10. Once in a desired position within the vein 10, the support device 1130 can be transitioned from the first configuration to the second configuration. As shown in FIGS. 13 and 14, in some instances, the support device 1130 can be positioned relative to the valve V such that the valve V is in contact with a portion of the support device 1130 that is closer to, for example, a longitudinal centerline L of the support device 1130 (FIG. 13) than one of the local minima or one of the local maxima. In other words, the valve V can be in contact with a portion of the support device that is approximately evenly spaced between a local minimum and an adjacent local maximum. In such instances, the support device 1130 can exert a force on the valve V to result in a first amount of displacement of the valve, as indicated by the arrows C in FIG. 13. That is to say, the support device 1130 can open the valve V a first amount, as shown in FIG. 14.

Figure 15:
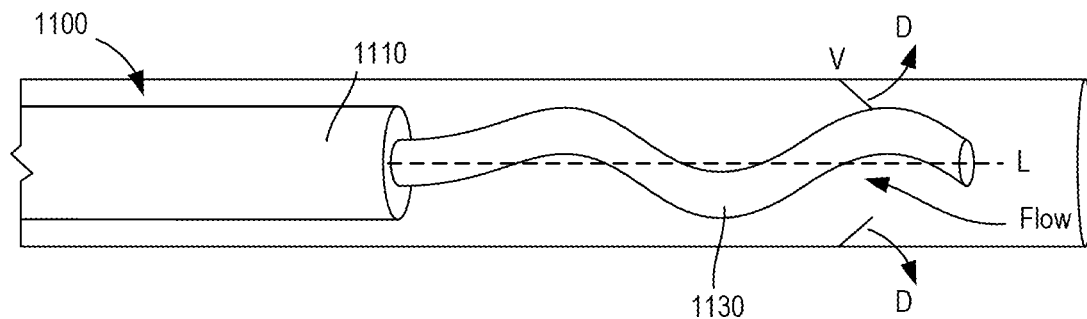
Figure 16:
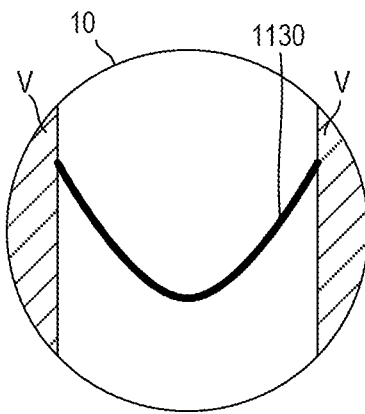

In other instances, the support device 1130 can be placed in a desired position within the vein 10 and transitioned from to the second configuration such that the valve V is in contact with a portion of the support device 1130 that is closer to, for example, a local maxima or a local minima than the longitudinal centerline L, as shown in FIGS. 15 and 16. In other words, the valve V can be in contact with a portion of the support device 1130 at or near one of a local maximum or at or near one of local minima. As such, the support device 1130 can exert a force on the valve V to result in a second amount of displacement (e.g., greater than the first amount of displacement), as indicated by the arrows DD in FIG. 15. That is to say, the support device 1130 can increase an amount that the valve V is open when the valve V is in contact with a portion of the support device 1130 that is closer to a local minimum or a local maximum than when the valve V is in contact with a portion of the support device 1130 that is closer to the longitudinal centerline L of the support device 1130 (e.g., as shown in FIG. 16).

Figure 17:
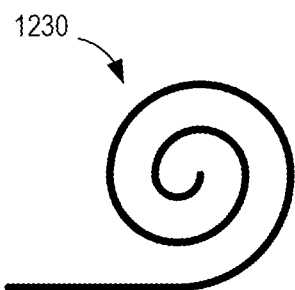
FIGS. 17-23 are schematic illustrations of various support devices in the second configuration each according to a different embodiment.
Figure 18:
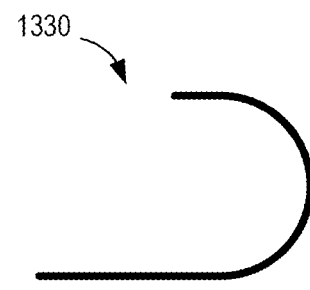
Figure 19:
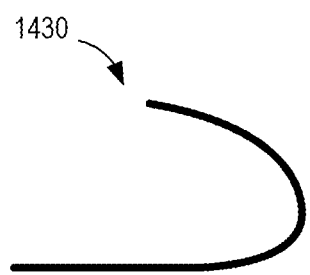
Figure 20:
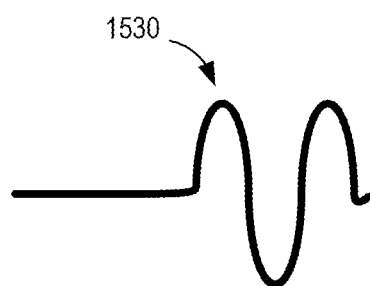
Figure 21:
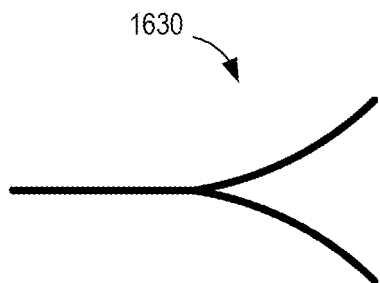
Figure 22:
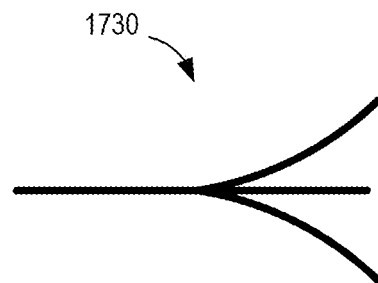
Figure 23:
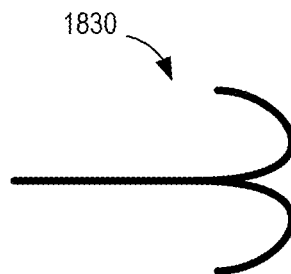

While the support devices 1030 and 1130 have been shown and described as forming and/or have a particular shape and/or arrangement when in the second configuration and/or state, it should be understood that the support devices 1030 and/or 1130 have been presented by way of example only and not limitation. As described above, a support device and/or a portion of the support device can be configured to have any suitable arrangement when placed in its second configuration and/or state. For example, FIGS. 17-23 are schematic illustrations of various support devices (or support members) each according to a different embodiment. Specifically, as shown in FIG. 17, a support device 1230 can have a spiral arrangement when placed in the second configuration. As shown in FIG. 18, a support device 1330 can have U-bend arrangement when placed in the second configuration. The U-bend arrangement can be similar to the arrangement described above with reference to the support device 930 but can have a larger (or smaller) radius of curvature. As shown in FIG. 19, a support device 1430 can form a bend that is similar to the U-bend of the support devices 930 and/or 1330 but that is not symmetrical and/or a bend that otherwise does not result in a 180° bend in the support device 1430. As shown in FIG. 20, a support device 1530 can form a sinusoidal wave at, for example, an end portion of the support device 1530. In other embodiments, can support device can form a spiral structure at an end portion thereof that can form a ball or conical shape. As shown in FIG. 21, a support device 1630 can have a Y-shaped arrangement when placed in the second configuration. As shown in FIG. 22, a support device 1730 can have a Y-shaped arrangement when placed in the second configuration that is similar to the Y-shaped arrangement of the support device 1630. The support device 1730, however, can include a first portion and a second portion forming the Y-shaped arrangement and can also include a third portion disposed between the first portion and the second portion. As shown in FIG. 23, a support device 1830 can have a first portion and a second portion that are each bent and/or deflected in a manner similar to that shown in FIGS. 18 and/or 19.

While specific examples of support devices configured to transition between a first and second configuration are shown and described above with reference to FIGS. 11-23, in other embodiments, a support device can be configured to have any suitable shape, size, and/or arrangement when placed in a second configuration and/or state. In some embodiments, the size, shape, and/or arrangement of such support devices when in the second configuration and/or state can be at least partially based on one or more characteristics of the portion of the body (e.g., a vein) that each support device is configured to support. For example, in some embodiments, a support device configured to support a vein (or other suitable structure) in the arm of an adult patient can be configured to form a spiral and/or can form a relatively large shape and/or size when in the second configuration. In other embodiments, a support device configured to support a vein (or other suitable structure) of a pediatric patient can be configured to have a relative small shape and/or size when in the second configuration or may not be configured to transition to a second configuration at all (e.g., as described above with reference to the support device 930).

While the support devices are described above with reference to FIGS. 9-23 as supporting a vein by transitioning a valve of the vein from a relatively closed state to a relatively open state to allow a sufficient flow of blood through the valve, in other embodiments, any of the support devices described herein can be used to support any suitable portion of the structure in which that support device is disposed. For example, in some embodiments, any of the support devices described above can be configured to support, for example, the walls of a vein to limit and/or substantially prevent a collapse of at least a portion of the vein (e.g., in response to a negative pressure resulting from aspiration). In other embodiments, any of the support devices described above can be used to support any portion or any combination of portions of the vein in which that support device is disposed. Moreover, in some instances, the transitioning of a support device from a first configuration to a second configuration can be operable in clearing, removing, and/or breaking up any debris, clot, or tissue within a portion of the vein that can otherwise at least partially restrict a flow of blood therethrough. Accordingly, while the support devices are described above as providing physical support to at least one of a catheter or a vein in which the catheter is disposed, in some instances, any of the support device described herein can provide support for and/or can otherwise facilitate the process of gaining access to a portion of a vein, the process of aspirating fluid from the vein, the process of delivering fluid to the vein, and/or any other suitable process.

Figure 24:
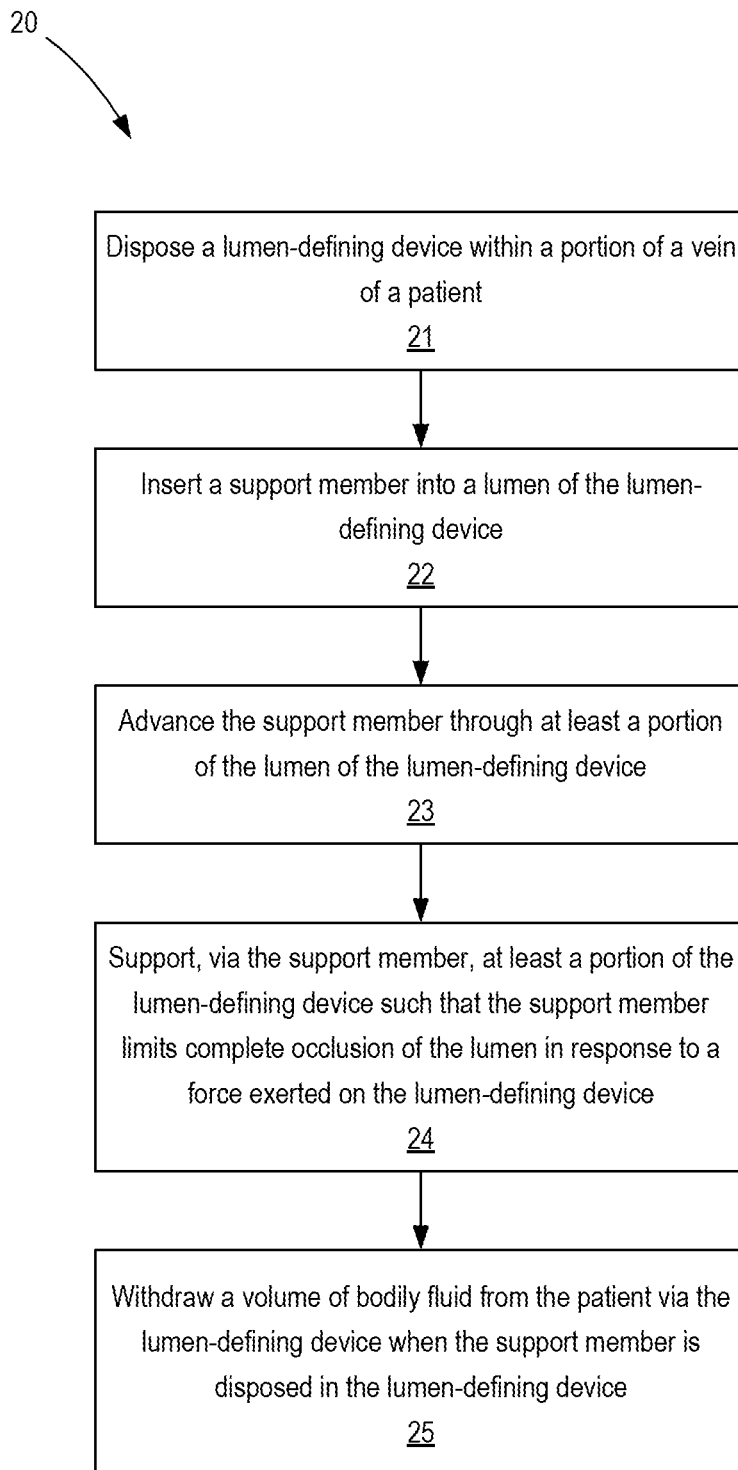
FIG. 24 is a flowchart illustrating a method of using a support device according to an embodiment.

FIG. 24 is a flowchart illustrating a method 20 of using a support device and/or support member according to an embodiment. The support device and/or support member (referred to henceforth as "support member") can be any suitable support member such as those described herein. In some implementations, for example, the support member can be similar to the support device 230 and/or the support member 235 described above with reference to FIGS. 2A-2D and can have any suitable shape, size, and/or configuration. As described in detail above, the support member can be configured to support at least a portion of a lumen-defining device such as, for example, a vascular access device and/or the like.

The method 20 includes disposing a lumen-defining device within a portion of a vein of a patient, at 21. For example, in some embodiments, the lumen-defining device can be a peripheral intravenous catheter (PIV) configured to be percutaneously inserted into a vein of a patient. In some instances, the lumen-defining device can be inserted such that at least a hub of the lumen-defining device is disposed outside of the body of the patient.

A support member is inserted into a lumen of the lumen-defining device, at 22. The support member can be any suitable support member such as those described above. In some embodiments, the support member can be substantially similar to the support device 230 and/or support member 235 and can have any suitable cross-sectional shape such as, for example, those described above with reference to the support members shown in FIGS. 3-8. The support member is advanced through at least a portion of the lumen of the lumen-defining device, at 23. For example, in some instances, the support member can be placed in a distal position such that a desired portion of the support member is disposed within the lumen of the lumen-defining device (e.g., within the catheter of a PIV). In some instances, the support member can be advanced a sufficient amount to extend through a portion of the lumen-defining device corresponding to a point along the lumen-defining device that is in line with and/or disposed on a similar plane as an insertion site on the skin of a patient. In other instances, the support member can be advanced through any suitable portion of the lumen-defining device. In some instances, the support member can be advanced through substantially the entire lumen-defining device.

At least a portion of the lumen-defining device is supported via the support member such that the support member limits complete occlusion of the lumen in response to a force exerted on the lumen-defining device, at 24. For example, in some instances, the support member can be disposed in the lumen of the lumen-defining device and can prevent kinking or closing off of the lumen in response to a force exerted on the lumen-defining device, as described above with reference to FIGS. 2C and 2D. In some embodiments, the support member can be a filament or the like that can have a diameter sufficient to prevent a portion of the lumen-defining device from kinking, pinching, and/or folding in response to being bent, moved, manipulated, etc.

The method 20 includes withdrawing a volume of bodily fluid from the patient via the lumen-defining device when the support member is disposed in the lumen-defining device, at 25. As described above with reference to the support device 230 and/or support member 235 shown in FIGS. 2A-2D, the support member can be disposed in the lumen-defining device and can have a size and/or cross-sectional shape that allows the support member to support the lumen-defining device without undesirably blocking (or without completely blocking) a flow of fluid through the lumen. In some embodiments, for example, the support member can be a relatively small filament that the can positioned within the lumen-defining device and configured to remain therein for a desired period of time. In such embodiments, the filament can have a diameter that is sufficiently large to support the lumen-defining device and/or to otherwise limit or prevent kinking of the lumen-defining device, yet sufficiently small to allow fluid to pass through the lumen of the lumen-defining device.

In some implementations, a fluid transfer device can be coupled to a hub or the like of the lumen-defining device while the support member (e.g., filament) is disposed within the lumen. In such implementations, a user can manipulate the fluid transfer device to withdraw the volume of bodily fluid and the support member can be configured to support the lumen-defining device as the bodily fluid is transferred. For example, in some instances, the support member can support the lumen-defining device to limit and/or substantially prevent at least a partial collapse of the lumen-defining device as a result of a negative pressure therein (e.g., a suction force exerted by the fluid transfer device). In other instances, the support member can support the lumen-defining device to limit and/or substantially prevent kinking in response to one or more bends, turns, and/or changes in angle resulting from being at least partially disposed within a vein. Moreover, in some instances, the support member can support the lumen-defining device in any of the ways described above with reference to, for example, the support devices 230, 330, 430, 530, 630, 730, and/or 830 described above.

Figure 25:
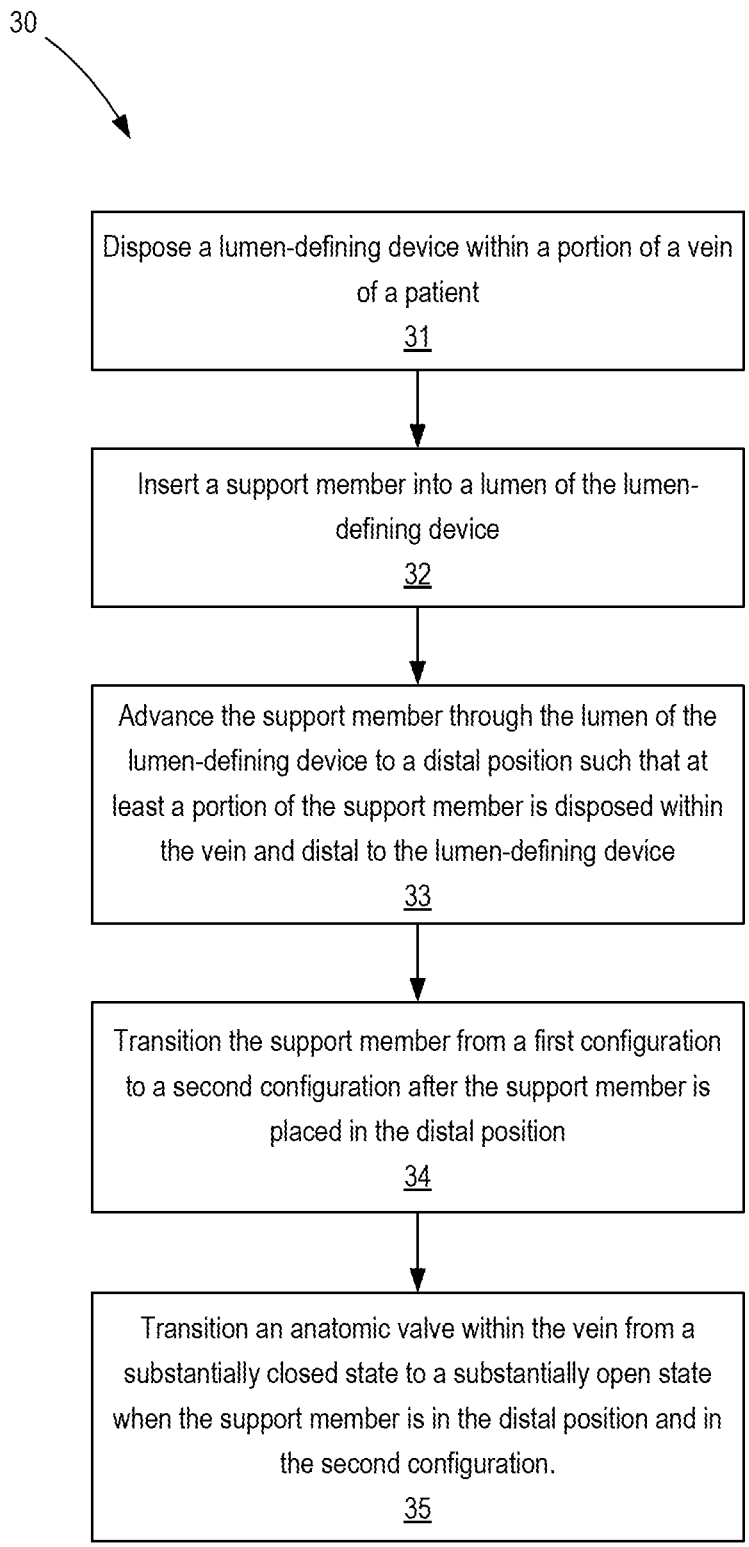
FIG. 25 is a flowchart illustrating a method of using a support device according to an embodiment.

FIG. 25 is a flowchart illustrating a method 30 of using a support device and/or a support member according to an embodiment. The support device and/or support member (referred to henceforth as "support member") can be any suitable support member such as those described herein. In some implementations, for example, the support member can be similar to the support members 930, 1030, 1130, 1230, 1330, 1430, 1530, 1630, 1730, and/or 1830. As described in detail above, in some implementations, the support member can be configured to support at least a portion of a lumen-defining device such as, for example, a vascular access device, and/or the like. In other implementations, the support member can be configured to support at least a portion of a vein or anatomic structure in which at least a portion of the support member is disposed.

The method 30 includes disposing a lumen-defining device within a portion of a vein of a patient, at 31. For example, in some embodiments, the lumen-defining device can be a peripheral intravenous catheter (PIV) configured to be percutaneously inserted into a vein of a patient. In some instances, the lumen-defining device can be inserted such that at least a hub of the lumen-defining device is disposed outside of the body of the patient.

A support member is inserted into a lumen of the lumen-defining device, at 32. The support member can be any suitable support member such as those described above. In some embodiments, the support member can be substantially similar to the support member 930, 1030, and/or 1130 described in detail above. In some embodiments, such a support member can be configured to transition between two or more states or configurations and can have and/or can form any suitable shape or configuration such as those described above with reference to the support members 1030, 1130, 1230, 1330, 1430, 1530, 1630, 1730, and/or 1830.

The support member is advanced through the lumen of the lumen-defining device to a distal position such that at least a portion of the support member is disposed within the vein and distal to the lumen-defining device, at 33. For example, in some instances, the support member can be placed in a distal position such that a desired portion of the support member is disposed within the vein (e.g., distal to a distal end portion of the lumen-defining device). In some instances, the support member can be advanced a sufficient amount to extend through a portion of the vein including and/or associated with an anatomic valve and/or the like. In some instances, the anatomic valve can be in a closed or at least partially closed state. For example, in some instances, the insertion of the lumen-defining device can result in vasoconstriction and/or in one or more valves of the vein transitioning to a closed or semi-closed (e.g., constricted state).

The support member is transitioned from a first configuration to a second configuration after the support member is placed in the distal position, at 34. For example, as described above, the distal position can be a position in which a desired portion of the support member extends beyond a distal end portion of the lumen-defining device to be disposed within the vein. As described above with reference to the support members 930, 1030, 1130, 1230, 1330, 1430, 1530, 1630, 1730, and/or 1830, the support member and/or a device coupled thereto can be engaged and/or manipulated in any suitable manner to transition the support member from the first state and/or configuration to the second state and/or configuration. In some embodiments, a distal end portion of the support member can have and/or can define a first area or perimeter when the support member is in the first configuration and can have and/or can define a second area or perimeter when the support member is in the second configuration. In some such embodiments, the second area and/or perimeter can be greater than the first area and/or perimeter, as described in detail above. In other embodiment, the support member can transition in any suitable manner and/or can assume or form any suitable shape when placed in the second state and/or configuration.

The method 30 further includes transitioning an anatomic valve within the vein from a substantially closed state to a substantially open state when the support member is in the distal position and in the second configuration, at 35. For example, in some instances, the support member can be inserted into the vein such that at least a portion the support member extends through the anatomic valve and/or other anatomic structure. In such instances, extending a portion of the support member through the anatomic valve (e.g., placing the support member in the distal position) can be configured to at least partially open the valve and/or otherwise place the valve in an at least partially open state and/or configuration. Moreover, in some instances, transitioning the support member to the second configuration can be such that an area or perimeter of at least the distal end portion of the support member is increased and thus, when placed in the second configuration, the support member can be configured to place the anatomic valve in an open state and/or configuration, as described in detail above with reference to the support members 930, 1030, 1130, 1230, 1330, 1430, 1530, 1630, 1730, and/or 1830.

While various embodiments have been described above, it should be understood that they have been presented by way of example only, and not limitation. Where schematics and/or embodiments described above indicate certain components arranged in certain orientations or positions and/or coupled to one or more other components, the arrangement of components may be modified. For example, while the support devices have been shown and/or described above as being coupled to and/or used with, for example, a peripheral intravenous catheter, in other embodiments, the devices can be coupled to any suitable access device, introducer, adapter, secondary or intermediate device, etc. For example, in some instances, a support device can be coupled to and/or used with an access device such as a PIV, a peripherally inserted central catheter (PICC), an introducer catheter, an arterial catheter, and/or the like. In addition, a support device can be used with any suitable adapter that may be coupled to the access device (e.g., a single port IV extension set, a dual port IV extension, a "Y-adapter," "T-adapter," a flow or fluid control valve, etc.). In some embodiments, the adapter, in turn, can be coupled to any suitable surgical or interventional device, a fluid transfer device, a fluid source, a fluid reservoir, an evacuated container, etc.

Although various embodiments have been described as having particular features and/or combinations of components, other embodiments are possible having a combination of any features and/or components from any of embodiments as discussed above. For example, in some embodiments, a support device can have any suitable cross-sectional shape such as, for example, those described above with reference to FIG. 3-8, and can be configured to form and/or be reconfigured to form any suitable shape (e.g., not a cross-sectional shape) such as, for example, those described above with reference to FIGS. 17-23.

While the embodiments have been particularly shown and described, it will be understood that various changes in form and details may be made. Any of the aspects and/or features of the embodiments shown and described herein can be modified to affect the performance of the support device and/or an access device being supported by the support device. For example, the shape, size, thickness, stiffness, etc. of a support device can be increased or decreased to increase or decrease, respectively, am amount of support provided. While support devices have been shown as having a particular size or shape, support devices having other sizes and/or shapes are possible. For example, a support device can be a wire or filament having a constant or varied diameter (e.g., circular cross-sectional shape). In other embodiments, a support device can have an oblong, oval, elliptical, square, rectangular, and/or any other suitable polygonal cross-sectional shape. By way of another example, any of the components of the support devices described herein can be formed from any suitable material or combination of materials that can result in a desired hardness, durometer, and/or stiffness of that component.

Moreover, while the support devices have been described above as including, for example, a single support device, device, filament, element, etc., in other embodiments, a support device can include one or more support devices. For example, in some embodiments, a support device can include two or more separate support devices or filaments. In such embodiments, the two or more separate support devices or filaments can be independently formed or can be formed with one or more portions that are monolithic or unitarily constructed. In such embodiments, the two or more support devices can be independently controlled or manipulated or collectively controlled or manipulated. While the support devices are shown and described herein as generally including one support member or filament, it should be understood that such embodiments are presented by way of example only and not limitation. Indeed, a support device can include any suitable number of support members, filaments, elements, and/or portions thereof. Moreover, such a support device can include any suitable combination of support members or filaments such as, for example, any suitable combination of the embodiments described herein.

The support devices described herein can be assembled during one or more manufacturing processes and packaged alone, in a set of multiple support devices, or in conjunction with an access device. For example, in some instances, a support device can be manufactured and/or assembled and an access device can be manufactured and/or assembled in one or more separate or collective processes. In some instances, the support device and the access device can be packaged together in a substantially sterile environment such as, for example, an ethylene oxide environment, or the like. In some instances, the support device can be preassembled with the access device or can be collectively packaged in a non-assembled arrangement. In some embodiments, the devices can be packaged with, for example, a PIV, an extension set, a Y-adapter or T-adapter, one or more additional support devices, and/or any other suitable component.

Where methods and/or schematics described above indicate certain events and/or flow patterns occurring in certain order, the ordering of certain events and/or flow patterns may be modified. Additionally, certain events may be performed concurrently in parallel processes when possible, as well as performed sequentially.

What is claimed:

1. An access device comprising:
   a lumen-defining device having a proximal end and a distal end, the lumen-defining device having an open end at the proximal end, and an open end at the distal end, and defining a lumen extending between the proximal end and the distal end;
   a support member having a proximal end and a distal end, the support member disposed within the lumen of the lumen-defining device; and
   a hub having a proximal end and a distal end, the distal end of the hub configured to be coupled to the proximal end of the lumen-defining device and the proximal end of the support member,
   wherein the support member and the lumen-defining device are flexible, and
   wherein, when the lumen-defining device and the support member are bent, the support member supports at least a portion of the lumen-defining device without occluding or blocking the entire lumen.

2. The access device of claim 1, wherein the lumen-defining device has a first stiffness and the support member has a second stiffness greater than the first stiffness.

3. The access device of claim 1, wherein the support member has an outer diameter that is smaller than an inner diameter of the lumen-defining device.

4. The access device of claim 3, wherein the lumen-defining device comprises a 16-gauge catheter.

5. The access device of claim 3, wherein the lumen-defining device comprises a 24-gauge catheter.

6. The access device of claim 1, wherein the support member is a solid elongate member having a circular cross-sectional shape.

7. The access device of claim 1, wherein the support member has an X-shaped cross-sectional shape.

8. The access device of claim 1, wherein the support member has a Y-shaped cross-sectional shape.

9. The access device of claim 1, wherein the support member has a C-shaped cross-sectional shape.

10. The access device of claim 1, wherein the support member has an I-shaped cross-sectional shape.

11. The access device of claim 1, wherein the support member has a Z-shaped cross-sectional shape.

12. An access device comprising:
    a lumen-defining device having a proximal end and a distal end, the lumen-defining device having an open end at the proximal end, and an open end at the distal end, and defining a lumen extending between the proximal end and the distal end;
    a support member having a proximal end and a distal end, the support member disposed within the lumen of the lumen-defining device; and
    a hub having a proximal end and a distal end, the distal end of the hub configured to be coupled to the proximal end of the lumen-defining device and the proximal end of the support member,
    wherein the support member and the lumen-defining device are flexible, and
    wherein the support member is transitionable from a first configuration in which a proximal end portion of the support member extends in a first direction to a second configuration in which the proximal end portion extends in a second direction.

13. The access device of claim 12, wherein the distal end portion of the support member forms a U-bend in the second configuration.

14. The access device of claim 12, wherein the distal end portion of the support member forms a spiral shape in the second configuration.

15. The access device of claim 12, wherein the distal end portion of the support member forms a wave shape in the second configuration.

16. The access device of claim 12, wherein the support member comprises more than one distal end portion and the distal end portions form a Y-shape in the second configuration.

17. The access device of claim 12, wherein the distal end portion of the support member is straight in the first configuration.

18. The access device of claim 12, wherein, when the lumen-defining device and the support member are bent, the support member supports at least a portion of the lumen-defining device without occluding or blocking the entire lumen.

19. The access device of claim 12, wherein the lumen-defining device has a first stiffness and the support member has a second stiffness greater than the first stiffness.

20. The access device of claim 12, wherein the support member has an outer diameter that is smaller than an inner diameter of the lumen-defining device.

* * * * *